(12) United States Patent
Wenk et al.

(10) Patent No.: US 7,847,123 B2
(45) Date of Patent: Dec. 7, 2010

(54) ANTIMICROBIAL COMPOSITIONS

(75) Inventors: Hans Henning Wenk, Essen (DE);
Petra Allef, Krefeld (DE); Stefan Bergfried, Essen (DE); Mike Farwick, Essen (DE); Burghard Grüning, Essen (DE)

(73) Assignee: Evonik Goldschmidt GmbH, Essen (DE)

(*) Notice: Subject to any disclaimer, the term of this patent is extended or adjusted under 35 U.S.C. 154(b) by 448 days.

(21) Appl. No.: 11/939,876

(22) Filed: Nov. 14, 2007

(65) Prior Publication Data
US 2008/0145320 A1 Jun. 19, 2008

(30) Foreign Application Priority Data
Nov. 14, 2006 (DE) ............ 10 2006 053 500

(51) Int. Cl.
*C07C 233/05* (2006.01)
*A61K 31/16* (2006.01)

(52) U.S. Cl. .......... 564/192; 514/625; 424/49; 424/65

(58) Field of Classification Search .......... 424/49, 424/65; 564/192; 514/625
See application file for complete search history.

(56) References Cited

U.S. PATENT DOCUMENTS

| | | | |
|---|---|---|---|
| 2,769,838 | A | 11/1956 | Matter et al. |
| 3,250,719 | A | 5/1966 | Schmolka et al. |
| 3,916,003 | A | 10/1975 | Suzuki et al. |
| 4,130,711 | A | 12/1978 | Shier |
| 4,195,096 | A | 3/1980 | Graham et al. |
| 4,525,288 | A | 6/1985 | Schlicht |
| 4,851,434 | A | 7/1989 | Deckner |
| 2005/0031580 | A1 | 2/2005 | Allef et al. |
| 2006/0165627 | A1 | 7/2006 | Allef et al. |
| 2006/0198859 | A1 | 9/2006 | Allef et al. |
| 2006/0204468 | A1 | 9/2006 | Allef et al. |
| 2007/0092470 | A1 | 4/2007 | Allef et al. |

FOREIGN PATENT DOCUMENTS

| | | |
|---|---|---|
| DE | 21 24 439 A1 | 12/1971 |
| DE | 26 31 284 A1 | 1/1978 |
| DE | 26 32 391 A1 | 1/1978 |
| DE | 27 29 209 A1 | 2/1978 |
| DE | 42 37 081 C2 | 5/1996 |
| DE | 42 40 674 C2 | 6/1999 |
| DE | 101 14 638 C1 | 3/2001 |
| DE | 102 26 942 A1 | 12/2003 |
| EP | 0 262 587 B1 | 1/1992 |
| EP | 0 769 291 A1 | 4/1997 |
| GB | 2 000 769 A | 1/1979 |
| JP | 07310093 | 11/1995 |
| JP | 09104671 | 4/1997 |
| JP | 9-227497 | * 9/1997 |
| JP | 2005-60457 | 3/2005 |
| WO | WO 90/09373 | 8/1990 |
| WO | WO 94/12467 | 6/1994 |
| WO | WO 95/00486 | 1/1995 |
| WO | WO 99/12420 | 3/1999 |
| WO | WO 02/30383 A2 | 4/2002 |
| WO | WO 2005/048709 | 6/2005 |
| WO | WO 2007/066164 A1 | 6/2007 |

OTHER PUBLICATIONS

Ratchford, J. of Organic Chemistry, 1950, 15, 326-332.*
William P. Ratchford, et al., "Preparation of N-Substituted Lactamides by Aminolysis of Methyl Lactate", J. Org. Chem. 1950, 15, 1950, pp. 317-235.
William P. Ratchford, "Preparation and Properties of N-n-Alkyl-lactamides", J. Org. Chem. 1950, 15, pp. 326-332.
XP-002471190, Database Beilstein, Beilstein Institute for Organic Chemistry.
Skinner, W. A. et al. "Tick Repellents I: Ethylene Glycol Acetamides" Journal of Pharmaceutical Sciences 71(7): 837-839 (1982).
XP-002471191, Chemical Abstracts Service, Pahoch, Miroslav, et al., "Membrane for ion-selective barium electrode".
XP-002471192, Chemical Abstracts Service, Uno, Mitsuru, et al., "Preparation of ether compounds as surfactants".
XP-002471193, Chemical Abstracts Service, Otawa, Yasunori, et al., "Preparation of tetra-alkyl ammonium salts as hair cosmetics".
XP-002471194, Chemical Abstracts Service, Shono, Tatsuya, et al., "Regioselectivity of enzymic 0-dealkylation of simple analogs of cholecystographic contrast media".
XP-002471195, Database Beilstein, Beilstein Institute for Organic Chemistry.
XP-002471196, Database Beilstein, Beilstein Institute for Organic Chemistry.
XP-002471197, Database Beilstein, Beilstein Institute for Organic Chemistry.
XP-002471198, Database Beilstein, Beilstein Institute for Organic Chemistry.
XP-002471264, Chemical Abstract Services, Yamamuro, Akira, et al., "Hydroxyfatty acids and their derivatives as inhibitors for secretion of sebum".

* cited by examiner

*Primary Examiner*—Shailendra Kumar
(74) *Attorney, Agent, or Firm*—Scully, Scott, Murphy & Presser, P.C.

(57) ABSTRACT

Compounds of the general formula $$R_1-\underset{H}{\overset{O(AO)_nR_5}{\underset{|}{C}}}-R_2-\overset{O}{\underset{\underset{R_3}{|}}{\overset{\|}{C}}}-N-R_4$$

and to the use thereof for controlling microorganisms are provided.

13 Claims, No Drawings

ANTIMICROBIAL COMPOSITIONS

FIELD OF THE INVENTION

The present invention relates to antimicrobial compositions, and to their use in cosmetic preparations.

BACKGROUND OF THE INVENTION

Antimicrobial active ingredients are used widely in cosmetic deodorants, antidandruff and antiacne formulations, footcare and personal hygiene compositions, and also oral hygiene and dental care products.

Body odor arises primarily when odorless perspiration is decomposed by microorganisms on the skin. Only the microbial degradation products cause the unpleasant sweat odor. This arises, in particular, where there is a high density of sweat glands and also a high density of odor-producing germs, such as, for example, in the armpits.

Certain skin diseases are also associated with excess growth of undesired microorganisms on the skin. Thus, acne is caused inter alia through uncontrolled growth of the anaerobic skin bacterium *Propionibacterium acnes*. Dandruff is connected inter alia with the fungus *Malassezia Furfur*.

In the oral hygiene sector, microorganisms play a significant role, for example in the formation of caries and dental plaque.

The effect of deodorants can be based on various mechanisms which, if appropriate, can also be combined:
- avoidance of sweat formation through antiperspirants, such as, for example, aluminum chlorohydrate (ACH) or aluminum zirconium tetrachlorohydrex GLY,
- prevention of odor formation through control of odor-forming microorganisms (in particular coryneforms),
- prevention of odor formation through inhibition of microbial enzymes which are responsible for odor formation from sweat,
- binding of odors which cause sweat odor by substances, e.g., by zinc compounds, such as zinc ricinoleate or salts thereof or by cyclodextrins,
- concealment of sweat odor by means of fragrances.

1. Antimicrobial Active Ingredients

The use of antimicrobial active ingredients in cosmetic formulations, in particular in cosmetic deodorants, is sufficiently known from the prior art.

In use, for example, is triclosan (5-chloro-2-(2,4-dichlorophenoxy)phenol), which exhibits an antimicrobial effect against a broad spectrum of microorganisms. On account of the broadband effect, triclosan has an adverse effect on the microflora of the skin. Furthermore, due to the specific mode of action, there is the risk of the formation of resistances.

DE 42 40 674 discloses a combination of glycerol monoalkyl ethers of the general formula

where R is a branched or unbranched $C_{6-18}$ alkyl group, with one or more further deodorizing active ingredients as a deodorant composition.

A disadvantage of these compounds is that they only have low solubility in aqueous systems and can only be formulated in such systems in combination with solubilizers. Furthermore, these substances also have a suppressing or germ-reducing effect on typical representatives of normal skin flora, e.g., *Staphylococcus epidermidis*, as a result of which the microbiological equilibrium on the skin can be permanently disturbed.

WO 02/30383 discloses antimicrobial deodorants which comprise a transition metal chelator as the active ingredient.

DE-A 42 37 081 describes cosmetic deodorants characterized by an effective content of monocarboxylic acid esters of di- or triglycerol. These prior art compounds have a specific suppression on the growth of odor-forming germs, but, on account of the ester bond, only have long-term stability in formulations within a restricted pH range.

EP 0 262 587 discloses N-octyl- and N-decylsalicylamide inter alia as an antimicrobial active ingredient in body deodorants. Other derivatives, in particular those based on aliphatic carboxylic acids, or alkoxylated derivatives are not described.

2. Amides in Cosmetic Formulations

Simple N-substituted lactic acid amides have been known for a long time. For example, Ratchford describes the synthesis of N-alkyl-, N-aryl- and N-alkenylamides of lactic acid ("Preparation of N-substituted lactamides by aminolysis of methyl lactate", J. Org. Chem. 1950, 15, 317 to 325; "Preparation and properties of N-alkyllactamides", J. Org. Chem. 1950, 15, 326 to 332) by reacting lactic acid or methyl lactate with alkylamines.

JP2005-060457 describes compounds of the general formula

where $R_1$ is a linear or branched $C_{6-21}$ alkyl radical, $R_2$ is a methyl, 1-hydroxyethyl or 1-hydroxy-1-methylethyl group, as thickeners in cosmetic formulations. An antimicrobial effect of the products is not described.

DE-A 26 31 284 provides cosmetic compositions with a content of amides of hydroxyalkanlecarboxylic acids of the general formula

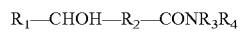

where $R_1=C_{1-4}$ alkyl, $R_2$ is a direct bond or $C_{1-3}$ alkylene (optionally alkyl- or hydroxy-substituted), $R_3$ and/or $R_4$, independently of one another, are $C_{1-4}$ alkyl or $C_{2-6}$ hydroxyalkyl having 1 to 5 OH groups.

In the cosmetic compositions of DE-A 26 31 284, the amides serve as humectants. An antimicrobial effect is not mentioned. Furthermore, neither longer-chain nor alkoxylated derivatives are described.

U.S. Pat. No. 3,916,003 describes nonionic surfactants of the formula

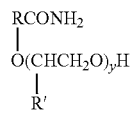

where R is an aliphatic hydrocarbon radical having 17 carbon atoms, the polyoxyalkylene chain is bonded at position 12 of the carbon chain, R' is a hydrogen atom or a short-chain alkyl radical, and y is a number from 1 to 50. Neither N-alkylated nor shorter-chain derivatives are described.

U.S. Pat. No. 4,851,434 describes compounds of the general structure

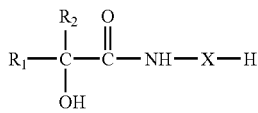

where $R_1$ and $R_2$ are H or short alkyl radicals, and X corresponds to one of the groups $(CH_2CH_2O)_n$, $(CH_2CH(CH_3)O)_n$, $(CH_2CH_2CH(CH_3)O)_n$ or $CH_2(CHOH)_4CH_2O$. The compounds disclosed in the '434 patent are described as humectants in cosmetic formulations. The substances differ in principle from the substances described in this application since the latter contain polyalkylene oxide groups on the amide nitrogen (not on the OH oxygen) and furthermore contain no simple N-alkyl radicals. Moreover, no antimicrobial or bacteriostatic properties are described in the '434 patent as well.

SUMMARY OF THE INVENTION

In view of the prior art mentioned above, there is a need for providing compounds which permit selective control of undesired microorganisms, in particular those which are established on the skin. Additionally, there is also a need for compounds which are stable in nonpolar and polar (in particular aqueous) systems, have good skin compatibility, and which have a good ability to be formulated in customary application forms, in particular cosmetic formulations.

In this connection, "control" is to be understood as meaning maintaining or reducing the germ count by suppressing the growth of the organisms, or killing them. "Selective" in this sense means that the controlling effect is more marked on undesired (e.g., odor-forming) germs than that on microorganisms of the normal skin flora. Undesired germs include, for example, Corynebacterium xerosis, Propionibacterium acnes, Malassezia furfur, but without being limited to these. "Microorganisms" are to be understood as meaning, in particular, bacteria and fungi (including yeasts). The expression "formulations" includes so-called "leave-on" products, such as creams, lotions, pump or aerosol sprays, wipes, deodorant sticks and roll-on formulations; "rinse-off" products such as shampoos, shower gels, liquid soaps, hair rinses and conditioners; oral hygiene products such as mouthwash solutions or toothpaste; cleaning products such as dishwashing compositions, household cleaners (floor, kitchen, bath cleaners), but without being limited to these.

Customary deodorants are supplied primarily in the form of roll-on dispensers, aerosols, pump sprays, deodorant sticks, dry deodorant sprays or wipes. Antimicrobial ingredients are used therein either as the sole active ingredient or in combination with other substances effective as antiperspirants or deodorants, such as, for example, triclosan, ethylhexylglycerol, aluminum chlorohydrate, aluminum zirconium tetrachlorohydrex GLY, aluminum zirconium pentachlorohydrate, farnesol, polyglycerol caprate or caprylate, triethyl citrate, penta(carboxymethyl)diethylenetriamine (pentetic acid), pentylene glycol, propylene glycol, ethanol, zinc ricinoleate, cyclodextrins or zinc oxide.

The spectrum of formulation bases ranges here from solid formulations via liquid or cream-like O/W or W/O emulsions to aqueous, alcoholic or oil-containing liquid systems. Furthermore, the formulations cover a large pH range, which can extend from about 3 to about 9.

This gives rise not only to high requirements on the stability of the active ingredient (in particular, no hydrolysis or alcoholysis should take place under the specified conditions), but also on the effectiveness, which should be as constant as possible over the entire pH range of the possible cosmetic formulations.

Surprisingly, it has now been found that compounds of the general formula (I) achieve the above-mentioned objects in an excellent manner.

The invention thus provides compounds of the general formula (I)

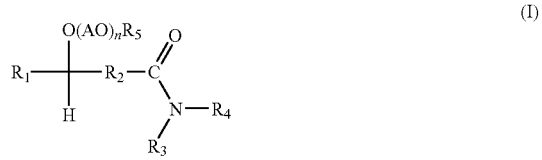

in which the substituents and indices have the following meaning:

$R_1$=H or a hydrocarbon radical having 1 to 18 carbon atoms which is optionally branched and/or contains multiple bonds and/or hydroxy groups and/or alkyl groups and/or hydroxyalkyl groups, preferably 1 to 10 carbon atoms, in particular 1 to 5 carbons atoms, $R_2$=a direct bond or a hydrocarbon radical having 1 to 18 carbon atoms which is optionally branched and/or contains multiple bonds and/or hydroxy groups and/or alkyl groups and/or hydroxyalklyl groups, preferably 1 to 6 carbon atoms, in particular 1 to 4 carbons atoms, $R_3$, $R_4$=independently of one another, H or a hydrocarbon radical having 1 to 18 carbon atoms which is optionally branched and/or contains multiple bonds and/or hydroxy groups and/or alkyl groups and/or hydroxyalkyl groups, preferably 4 to 12 carbon atoms, in particular 6 to 10 carbon atoms, $R_5$=H or $C_1$-$C_4$-acyl radical, AO=at least one radical selected from the group $-CH_2CH_2O-$, $-CH_2CHR_6O-$, $-CHR_6CH_2O-$, and $-CH_2CH_2OHCH_2O-$ where $R_6$=$C_1$-$C_4$-alkyl, n=1 to 20, preferably 1 to 10, in particular 2 to 5, based on the mean value of all oligomers, with the proviso that $R_3$ and $R_4$ are not H at the same time and the sum of the carbon atoms in $R_3$ and $R_4$ is not greater than 18 and that the sum of the carbon atoms in $R_1$, $R_2$, $R_3$ and $R_4$ does not exceed 36.

The invention further provides the use of compounds of the general formula (Ia)

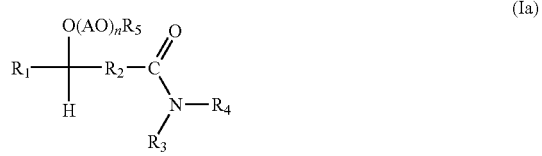

in which the substituents and indices have the following meaning:

$R_1$=H or a hydrocarbon radical having 1 to 18 carbon atoms which is optionally branched and/or contains multiple bonds and/or hydroxy groups and/or alkyl groups and/or hydroxyalkyl groups, preferably 1 to 10 carbon atoms, in particular 1 to 5 carbon atoms, $R_2$ = a direct bond or a hydrocarbon radical having 1 to 18 carbon atoms which is optionally branched and/or contains multiple bonds and/or hydroxy groups and/or alkyl groups and/or hydroxyalkyl groups, preferably 1 to 6 carbon atoms, in particular 1 to 4 carbon atoms, $R_3$, $R_4$ = independently of one another, H or a hydrocarbon radical having 1 to 18 carbon atoms which is optionally branched and/or contains multiple bonds and/or hydroxy groups and/or alkyl groups and/or hydroxyalkyl groups, preferably 4 to 12 carbon atoms, in particular 6 to 10 carbon atoms, $R_5$ = H or $C_1$-$C_4$-acyl radical, AO = at least one radical selected from the group —$CH_2CH_2O$—, —$CH_2CHR_6O$—, —$CHR_6CH_2O$—, and —$CH_2CH_2OHCH_2O$— where $R_6$=$C_1$-$C_4$-alkyl, n=0 to 20, preferably 0 to 10, in particular 0 to 5, based on the mean value of all oligomers, with the proviso that $R_3$ and $R_4$ are not H at the same time and the sum of the carbon atoms in $R_3$ and $R_4$ is not greater than 18 and that the sum of the carbon atoms in $R_1$, $R_2$, $R_3$ and $R_4$ does not exceed 36, for controlling microorganisms.

DETAILED DESCRIPTION OF THE INVENTION

As stated above, the invention relates to compounds of general formula I mentioned above and the use of compounds of general formula Ia for controlling microorganisms.

Compounds that can be used according to the invention are, for example, compounds of the general formula (I) based on glycolic acid, hydroxybutyric acids, hydroxyvaleric acids, hydroxycaproic acids and, in particular, lactic acid.

According to the invention, highly preferred compounds are those wherein n=0, $R_5$=H, $R_1$=$CH_3$, $R_2$ is a direct bond, $R_3$=H and $R_4$=$C_4$-$C_{12}$—, preferably $C_8$-alkyl radical.

According to the invention, even more preference is given to compounds wherein n is ≧1, $R_5$=H or acyl, $R_1$=$CH_3$, $R_2$ is a direct bond, $R_3$=H and $R_4$=$C_4$-$C_{12}$—, preferably $C_8$-alkyl radical.

In particular, these compounds permit selective control of undesired microorganisms on the skin and skin appendages without greatly influencing the normal flora present.

The compounds of the invention are stable to hydrolysis over a large pH range and can be incorporated into various cosmetic standard formulations without problems. Moreover, the effectiveness of the compounds of the invention has no noteworthy dependence on the pH, which is a further advantage of the compounds of the invention; i.e., the invention compounds thus have universal applicability.

The preparation of nonalkoxylated lactic acid derivatives by amidation of lactic acid or alkyl lactates with alkylamines is sufficiently described in the literature (cf. e.g., "Preparation of N-substituted lactamides by aminolysis of methyl lactate", J. Org. Chem. 1950, 15, 317-325; "Preparation and properties of N-alkyllactamides", J. Org. Chem. 1950, 15, 326-332).

Correspondingly, amides of other hydroxycarboxylic acid derivatives can also be prepared by reacting the carboxylic acids or their alkyl esters or lactones with primary or secondary amines.

Hydroxycarboxylic acid units which may be used are, for example, lactic acid, glycolic acid, 2-hydroxybutyric acid, 4-hydroxybutyric acid, 6-hydroxyhexanoic acid, 2,2-dimethylolpropionic acid, 3,3-dimethyl-2,4-dihydroxybutyric acid or $C_1$-$C_4$-alkylesters thereof, particular preference being given to lactic acid or ethyl lactate. For example, the lactones of 4-hydroxybutyric acid or 6-hydroxyhexanoic acid can also be used.

Suitable amines are primary or secondary aliphatic amines, such as, for example, n-hexyl-, n-octyl-, n-decylamine, n-dodecylamine, 2-ethylhexylamine, ethanolamine or diethanolamine, preference is given to acyclic, primary aliphatic amines (branched or unbranched) and, in particular n-hexylamine, n-octylamine, n-decylamine, n-dodecylamine or 2-ethylhexylamine.

The nonalkoxylated hydroxycarboxamides can be converted to the corresponding alkoxylated derivatives by reaction with one or more alkylene oxides or glycidol (in particular ethylene oxide or propylene oxide or mixtures of the two) at elevated temperature and under pressure, if appropriate in the presence of suitable catalysts. This always produces a distribution of different polyalkylene oxide chains whose mean value can be controlled through the molar excess of alkylene oxide used. It is known to the person skilled in the art that the oxyalkylene units may be distributed blockwise or are present in the form of a mixture with a distribution which is essentially regulated by statistical laws. A fraction of polyalkylene oxide, which preferably remains in the product, always forms as by-product. The catalyst used can be neutralized after the reaction by suitable additives. When using KOH or NaOH as catalyst, organic or inorganic acids, for example, are suitable, particularly advantageously organic acids such as citric acid or lactic acid and those hydroxy carboxylic acids which have been used in the form of the amides in the reaction.

The compounds according to the invention can be used in a large number of formulations for uses in the home, industry, pharmacy and cosmetics. The compounds of the invention are particularly suitable as effective components in deodorants, which may be present in the form of aerosol sprays, pump sprays, roll-on formulations, deodorant sticks, W/O or O/W emulsions (e.g. creams or lotions) or wipes. The active ingredients/active ingredient combinations known from the prior art can be co-used in these formulations, such as, for example, triclosan, ethylhexylglycerol, aluminum chlorohydrate, aluminum zirconium tetrachlorohydrex GLY, aluminum zirconium pentachlorohydrate, farnesol, polyglycerol caprate or caprylate, triethyl citrate, penta(carboxymethyl)diethylenetriamine (pentetic acid), pentylene glycol, propylene glycol, ethanol, zinc ricinoleate, cyclodextrins or zinc oxide.

However, application is not restricted to use in deodorants, but may be advantageous wherever control of microorganisms or of their growth is desired, such as, for example, in personal hygiene articles, antiacne or antidandruff products, which may be present in the form of the customary leave-on or rinse-off formulations, such as, for example, creams, lotions, shampoos, washing solutions, hair rinses, wipes and similar formulations.

For antiacne products, the substances according to the invention can, if appropriate, also be used in combination with known antiacne active ingredients, such as, for example, dibenzoyl peroxide, salicylic acid, phytosphingosine, tretinoin, isotretinoin or plant extracts. Likewise, in the case of antidandruff products, combinations with known antidandruff active ingredients, such as, for example, climbazole, zinc pyrethione, selenium compounds (for example selenium sulfide), piroctone olamine (octopirox) or plant extracts, can be used.

The substances according to the invention can also be used in the oral hygiene product sector, in which case use in mouthwash solutions or toothpastes, in particular, is recommended.

The compounds of the invention can also be used in combination with other active ingredients which have in areas effectiveness gaps in which the substances according to the invention are effective, for this purpose. Thus, the use of preservatives can be reduced or, in some instances, classic preservatives can even be dispensed with completely.

The following non-limiting examples are provided to illustrate the present invention and to demonstrate some advantages of the inventive compounds in the area of cosmetic preparations.

Explanation of the raw materials used:

| Trade name | INCI name | Manufacturer |
|---|---|---|
| TEGO ® SML 20 | Polysorbate 20 | Goldschmidt GmbH |
| ABIL ® B 8832 | Bis-PEG/PPG-20/20 Dimethicone | Goldschmidt GmbH |
| Tegosoft ® GC | PEG-7 Glyceryl Cocoate | Goldschmidt GmbH |
| Reach ® 501 | Aluminium Chlorohydrate | Reheis, Inc. |
| Kathon ™ CG | Methylchloroisothiazolinone and Methylisothiazolinone | Rohm and Haas |
| Tegosoft ® M | Isopropyl Myristate | Goldschmidt GmbH |
| Allantoin | Allantoin | Fluka |
| Panthenol | Panthenol | Roche |
| Walocel ® HM 4000 | Hydroxypropylmethyl-cellulose | Wolff Cellulosics |
| Tylose ® H4000 | Hydroxyethylcellulose | Clariant |
| Teginacid ® H | Glyceryl Stearate and Ceteth-20 | Goldschmidt GmbH |
| TEGO ® Alkanol 18 | Stearyl Alcohol | Goldschmidt GmbH |
| Tegosoft ® Liquid | Cetearyl Ethylhexanoate | Goldschmidt GmbH |
| Tegosoft ® CT | Caprylic/Capric Triglyceride | Goldschmidt GmbH |
| TEGO ® Alkanol S2P | Steareth-2 | Goldschmidt GmbH |
| TEGO ® Alkanol S20P | Steareth-20 | Goldschmidt GmbH |
| Varonic ® APS | PPG-11 Stearyl Ether | Goldschmidt GmbH |
| ABIL ® 350 | Dimethicone | Goldschmidt GmbH |
| Tegosoft ® PBE | PPG-14 Butyl Ether | Goldschmidt GmbH |
| Tegosoft ® P | Isopropyl Palmitate | Goldschmidt GmbH |
| TEGO ® Alkanol L4 | Laureth-4 | Goldschmidt GmbH |
| Micro-Dry ® Ultrafine | Aluminium Chlorohydrate | Reheis, Inc. |

EXAMPLE 1

Preparation of N-octyllactamide 388 g (3 mol) of n-octylamine were added to 473 g (4 mol) of ethyl lactate in a round-bottomed flask with a distillation apparatus over the course of two hours with stirring and a nitrogen purge. When the addition was complete, the temperature was increased to 90° C. and the ethanol which formed was distilled. The temperature was then increased to 140° C. and maintained for one hour. The pressure was then reduced to 50 mbar and unreacted ethyl lactate was distilled. 585 g of octllactamide were obtained as a clear, pale pink-colored liquid. $^1$H-NMR (400 MHz, CDCl$_3$): 0.8 ppm (3H), 1.2 ppm (10H), 1.4 ppm (3H), 1.5 ppm (2H), 3.2 ppm (2H), 4.0 ppm (0.8H, br), 4.2 ppm (1H), 6.8 ppm (1H).

EXAMPLES 2 TO 4

Preparation of Further N-n-alkyllactamides

N-Hexyllactamide, N-heptyllactamide and N-nonyllactamide were prepared in accordance with example 1 by amidation of ethyl lactate with n-hexylamine, n-heptylamine and n-nonylamine, respectively.

EXAMPLE 5

Preparation of octyl-N-(2-ethylhexyl)lactamide

N-(2-Ethylhexyl)lactamide was prepared in accordance with example 1 by amidation of ethyl lactate with 2-ethylhexylamine.

EXAMPLE 6

Preparation of N-octylglycolamide 0.75 mol of glycolic acid were melted at 80° C., then 1.11 mol of octylamine were added dropwise with stirring. After the exothermic reaction had subsided, the mixture was heated for one hour to 165° C. and then the excess amine was distilled off under reduced pressure. The product was obtained after cooling in the form of a white, crystalline solid.

EXAMPLE 7

Preparation of N-octyl-4-hydroxybutyramide 1 mol of octylamine was heated to 100° C. with stirring. 1 mol of gamma-butyrolactone was added dropwise over a period of 30 minutes. The mixture was heated for three hours to 120° C. At the end of the reaction, a vacuum of 50 mbar was applied. The product was obtained after cooling in the form of a pale yellow solid.

EXAMPLE 8

Preparation of PEG-3-octyllactamide 100 g of N-octyllactamide were admixed with 1 g of 45% KOH in a pressurized reactor and dried for one hour at 115° C. and reduced pressure. Then, at 130° C., 3 mol equivalents of ethylene oxide were metered in over 40 minutes and the product was kept for a further 45 minutes at this temperature for a post reaction time. After cooling to room temperature, the mixture was neutralized with lactic acid. The product was obtained in the form of a clear, brownish liquid. Using $^1$H-NMR analysis, an addition of 3.1 mol of ethylene oxide per mol of octyllactamide was determined.

EXAMPLE 9

Preparation of PEG-10-octyllactamide 100 g of N-octyllactamide were admixed with 1 g of 45% KOH in a pressurized reactor and dried for one hour at 115° C. and reduced pressure. Then, at 130° C., 10 mol equivalents of ethylene oxide were metered in over 70 minutes and the product was kept at this temperature for a further 60 minutes for a post reaction time. After cooling to room temperature, the mixture was neutralized with lactic acid. Using $^1$H-NMR analysis, an addition of 10.9 mol of ethylene oxide per mol of octyllactamide was determined.

EXAMPLE 10

Antimicrobial Effect 20 ml of a 0.3% by weight solution of the test substance listed below in the table in water was inoculated with 200 μl of a fresh 48 hour culture of *C. xerosis* or *S. epidermidis* and incubated for three days at 37° C. Directly after the addition, as well as after 1, 3, 24 and 48 hours, samples, each of 1 ml, were taken and the germ count was determined.

| Test substance | Microorganism | CFU/ml Hours | | | | |
|---|---|---|---|---|---|---|
| | | 0 | 1 | 3 | 24 | 48 |
| Octyllactamide | *C. xerosis* | 9.1E+5 | 1.5E+4 | <2.0E+2 | <2.0E+2 | <2.0E+2 |
| | *S. epidermidis* | 1.9E+7 | 3.7E+6 | 3.0E+6 | 2.3E+6 | 8.5E+5 |
| Hexyllactamide | *C. xerosis* | 2.5E+6 | 5.5E+5 | 2.6E+3 | <2.0E+2 | <2.0E+2 |
| | *S. epidermidis* | 8.6E+6 | 1.7E+6 | 7.1E+5 | <2.0E+2 | <2.0E+2 |
| Octyl-PEG-3-lactamide | *C. xerosis* | 9.1E+5 | 6.3E+4 | 3.7E+3 | <2.0E+2 | <2.0E+2 |
| | *S. epidermidis* | 1.9E+7 | 4.1E+6 | 3.1E+6 | <2.0E+2 | <2.0E+2 |
| Octyl-PEG-10-lactamide | *C. xerosis* | 9.1E+5 | 4.5E+5 | 1.8E+5 | 1.6E+3 | <2.0E+2 |
| | *S. epidermidis* | 1.9E+7 | 2.3E+6 | 9.3E+6 | 8.1E+4 | <2.0E+2 |

EXAMPLE 11 pH Dependency of the Antimicrobial Effect

The antimicrobial effect of octyllactamide in buffered solutions was tested correspondingly to example 8 at various pH values.

| Substance | Micoorganism | CFU/ml Hours | | | | |
|---|---|---|---|---|---|---|
| | | 0 | 1 | 3 | 24 | 48 |
| Octyllactamide, pH 4.5 | *C. xerosis* | 1.0E+6 | 5.5E+4 | <2.0E+2 | <2.0E+2 | <2.0E+2 |
| | *S. epidermidis* | 3.7E+6 | 2.1E+6 | 7.9E+4 | <2.0E+2 | <2.0E+2 |
| Octyllactamide, pH 5.5 | *C. xerosis* | 1.0E+6 | 1.8E+5 | 3.5E+4 | <2.0E+2 | <2.0E+2 |
| | *S. epidermidis* | 3.7E+6 | 1.7E+6 | 4.7E+3 | <2.0E+2 | <2.0E+2 |
| Octyllactamide, pH 6.9 | *C. xerosis* | 7.3E+5 | 3.3E+3 | <2.0E+2 | <2.0E+2 | <2.0E+2 |
| | *S. epidermidis* | 3.1E+6 | 1.5E+6 | 5.7E+4 | <2.0E+2 | <2.0E+2 |

EXAMPLE 12

Pump Spray Deodorant Formulations without Ethanol

| | PS-1 | PS-2 | PS-3 | PS-4 | PS-5 | PS-6 | PS-7 | PS-8 |
|---|---|---|---|---|---|---|---|---|
| Phase A | | | | | | | | |
| Example 1 | 0.3 | 1.0 | — | — | 0.3 | 1.0 | — | — |
| Example 8 | — | — | 0.3 | 1.0 | — | — | 0.3 | 1.0 |
| TEGO ® SML 20 | 3.0 | 4.0 | 3.0 | 4.0 | 3.0 | 4.0 | 3.0 | 4.0 |
| Fragrance | 0.5 | 0.5 | 0.5 | 0.5 | 0.5 | 0.5 | 0.5 | 0.5 |
| Ethanol | — | — | — | — | — | — | — | — |
| ABIL ® B 8832 | 0.5 | 0.5 | 0.5 | 0.5 | 0.5 | 0.5 | 0.5 | 0.5 |
| Tegosoft ® M | — | — | — | — | — | — | — | — |

-continued

|  | PS-1 | PS-2 | PS-3 | PS-4 | PS-5 | PS-6 | PS-7 | PS-8 |
|---|---|---|---|---|---|---|---|---|
| Phase B | | | | | | | | |
| Water | ad 100 | ad 100 | ad 100 | ad 100 | ad 100 | ad 100 | ad 100 | ad 100 |
| Allantoin | 0.2 | 0.2 | 0.2 | 0.2 | 0.2 | 0.2 | 0.2 | 0.2 |
| Panthenol | 0.1 | 0.1 | 0.1 | 0.1 | 0.1 | 0.1 | 0.1 | 0.1 |
| Tegosoft ® GC | 1.0 | 1.0 | 1.0 | 1.0 | 1.0 | 1.0 | 1.0 | 1.0 |
| Phase C | | | | | | | | |
| Reach ® 501 | — | — | — | — | 30.0 | 30.0 | 30.0 | 30.0 |
| Kathon ™ CG | 0.03 | 0.03 | 0.03 | 0.03 | 0.03 | 0.03 | 0.03 | 0.03 |

EXAMPLE 13

Pump Spray Deodorant Formulations with Ethanol

|  | PS-9 | PS-10 | PS-11 | PS-12 | PS-13 | PS-14 | PS-15 | PS-16 |
|---|---|---|---|---|---|---|---|---|
| Phase A | | | | | | | | |
| Example 1 | 0.3 | 1.0 | — | — | 0.3 | 1.0 | — | — |
| Example 8 | — | — | 0.3 | 1.0 | — | — | 0.3 | 1.0 |
| TEGO ® SML 20 | 3.0 | 4.0 | 3.0 | 4.0 | 3.0 | 4.0 | 3.0 | 4.0 |
| Fragrance | 0.5 | 0.5 | 0.5 | 0.5 | 0.5 | 0.5 | 0.5 | 0.5 |
| Ethanol | ad 100 | ad 100 | ad 100 | ad 100 | 30.0 | 30.0 | 30.0 | 30.0 |
| ABIL ® B 8832 | — | — | — | — | — | — | — | — |
| Tegosoft ® M | 1 | 1 | 1 | 1 | — | — | — | — |
| Phase B | | | | | | | | |
| Water | — | — | — | — | ad 100 | ad 100 | ad 100 | ad 100 |
| Allantoin | — | — | — | — | — | — | — | — |
| Panthenol | — | — | — | — | — | — | — | — |
| Tegosoft ® GC | — | — | — | — | — | — | — | — |
| Phase C | | | | | | | | |
| Reach ® 501 | — | — | — | — | 20.0 | 20.0 | 20.0 | 20.0 |
| Kathon ™ CG | 0.03 | 0.03 | 0.03 | 0.03 | 0.03 | 0.03 | 0.03 | 0.03 |

EXAMPLE 14

Roll-On Deodorant Formulations without Ethanol

|  | RO-1 | RO-2 | RO-3 | RO-4 | RO-5 | RO-6 | RO-7 | RO-8 |
|---|---|---|---|---|---|---|---|---|
| Phase A | | | | | | | | |
| Example 1 | 0.3 | 1.0 | — | — | 0.3 | 1.0 | — | — |
| Example 8 | — | — | 0.3 | 1.0 | — | — | 0.3 | 1.0 |
| TEGO ® SML 20 | 3.0 | 4.0 | 3.0 | 4.0 | 3.0 | 4.0 | 3.0 | 4.0 |
| Fragrance | 0.5 | 0.5 | 0.5 | 0.5 | 0.5 | 0.5 | 0.5 | 0.5 |
| Ethanol | — | — | — | — | — | — | — | — |
| ABIL ® B 8832 | 1.0 | 1.0 | 1.0 | 1.0 | 1.0 | 1.0 | 1.0 | 1.0 |
| Tegosoft ® GC | — | — | — | — | — | — | — | — |
| Phase B | | | | | | | | |
| Water | ad 100 | ad 100 | ad 100 | ad 100 | ad 100 | ad 100 | ad 100 | ad 100 |
| Walocel ® HM 4000 | 0.7 | 0.7 | 0.7 | 0.7 | 0.7 | 0.7 | 0.7 | 0.7 |
| Tylose ® H4000 | — | — | — | — | — | — | — | — |
| Water (for swelling) | 34.3 | 34.3 | 34.3 | 34.3 | 34.3 | 34.3 | 34.3 | 34.3 |
| Allantoin | — | — | — | — | 0.2 | 0.2 | 0.2 | 0.2 |
| Panthenol | — | — | — | — | 0.1 | 0.1 | 0.1 | 0.1 |

-continued

|  | RO-1 | RO-2 | RO-3 | RO-4 | RO-5 | RO-6 | RO-7 | RO-8 |
|---|---|---|---|---|---|---|---|---|
| Phase C |  |  |  |  |  |  |  |  |
| Reach ® 501 | — | — | — | — | 20.0 | 20.0 | 20.0 | 20.0 |
| Kathon ™ CG | 0.03 | 0.03 | 0.03 | 0.03 | 0.03 | 0.03 | 0.03 | 0.03 |

EXAMPLE 15

Roll-On Deodorant Formulations with Ethanol

|  | RO-9 | RO-10 | RO-11 | RO-12 | RO-13 | RO-14 | RO-15 | RO-16 |
|---|---|---|---|---|---|---|---|---|
| Phase A |  |  |  |  |  |  |  |  |
| Example 1 | 0.3 | 1.0 | — | — | 0.3 | 1.0 | — | — |
| Example 8 | — | — | 0.3 | 1.0 | — | — | 0.3 | 1.0 |
| TEGO ® SML 20 | 3.0 | 4.0 | 3.0 | 4.0 | 3.0 | 4.0 | 3.0 | 4.0 |
| Fragrance | 0.5 | 0.5 | 0.5 | 0.5 | 0.5 | 0.5 | 0.5 | 0.5 |
| Ethanol | 20.0 | 20.0 | 20.0 | 20.0 | 20.0 | 20.0 | 20.0 | 20.0 |
| ABIL ® B 8832 | 0.5 | 0.5 | 0.5 | 0.5 | 0.5 | 0.5 | 0.5 | 0.5 |
| Tegosoft ® GC | 1.0 | 1.0 | 1.0 | 1.0 | 1.0 | 1.0 | 1.0 | 1.0 |
| Phase B |  |  |  |  |  |  |  |  |
| Water | ad 100 | ad 100 | ad 100 | ad 100 | ad 100 | ad 100 | ad 100 | ad 100 |
| Walocel ® HM 4000 | 0.7 | 0.7 | 0.7 | 0.7 | — | — | — | — |
| Tylose ® H4000 | — | — | — | — | 0.75 | 0.75 | 0.75 | 0.75 |
| Water (for swelling) | 36.75 | 36.75 | 36.75 | 36.75 | 36.75 | 36.75 | 36.75 | 36.75 |
| Allantoin | 0.1 | 0.1 | 0.1 | 0.1 | 0.1 | 0.1 | 0.1 | 0.1 |
| Panthenol | 0.2 | 0.2 | 0.2 | 0.2 | 0.2 | 0.2 | 0.2 | 0.2 |
| Phase C |  |  |  |  |  |  |  |  |
| Reach ® 501 | — | — | — | — | — | — | — | — |
| Kathon ™ CG | 0.03 | 0.03 | 0.03 | 0.03 | 0.03 | 0.03 | 0.03 | 0.03 |

|  | RO-17 | RO-18 | RO-19 | RO-20 | RO-21 | RO-22 | RO-23 | RO-24 |
|---|---|---|---|---|---|---|---|---|
| Phase A |  |  |  |  |  |  |  |  |
| Example 1 | 0.3 | 1.0 | — | — | 0.3 | 1.0 | — | — |
| Example 8 | — | — | 0.3 | 1.0 | — | — | 0.3 | 1.0 |
| TEGO ® SML 20 | 3.0 | 4.0 | 3.0 | 4.0 | 3.0 | 4.0 | 3.0 | 4.0 |
| Fragrance | 0.5 | 0.5 | 0.5 | 0.5 | 0.5 | 0.5 | 0.5 | 0.5 |
| Ethanol | 20.0 | 20.0 | 20.0 | 20.0 | 20.0 | 20.0 | 20.0 | 20.0 |
| ABIL ® B 8832 | 0.5 | 0.5 | 0.5 | 0.5 | 0.5 | 0.5 | 0.5 | 0.5 |
| Tegosoft ® GC | 1.0 | 1.0 | 1.0 | 1.0 | 1.0 | 1.0 | 1.0 | 1.0 |
| Phase B |  |  |  |  |  |  |  |  |
| Water | ad 100 | ad 100 | ad 100 | ad 100 | ad 100 | ad 100 | ad 100 | ad 100 |
| Walocel | 0.7 | 0.7 | 0.7 | 0.7 | — | — | — | — |
| Hydroxyethyl cellulose | — | — | — | — | 0.75 | 0.75 | 0.75 | 0.75 |
| Water (for swelling) | 36.75 | 36.75 | 36.75 | 36.75 | 36.75 | 36.75 | 36.75 | 36.75 |
| Allantoin | 0.1 | 0.1 | 0.1 | 0.1 | 0.1 | 0.1 | 0.1 | 0.1 |
| Panthenol | 0.2 | 0.2 | 0.2 | 0.2 | 0.2 | 0.2 | 0.2 | 0.2 |
| Phase C |  |  |  |  |  |  |  |  |
| Reach ® 501 | 20.0 | 20.0 | 20.0 | 20.0 | 20.0 | 20.0 | 20.0 | 20.0 |
| Kathon ™ CG | 0.03 | 0.03 | 0.03 | 0.03 | 0.03 | 0.03 | 0.03 | 0.03 |

EXAMPLE 16

Pump Spray Emulsions

|  | PE-1 | PE-2 | PE-3 | PE-4 | PE-5 | PE-6 | PE-7 | PE-8 |
|---|---|---|---|---|---|---|---|---|
| Phase A |  |  |  |  |  |  |  |  |
| Example 1 | 0.3 | 1.0 | — | — | 0.3 | 1.0 | — | — |
| Example 8 | — | — | 0.3 | 1.0 | — | — | 0.3 | 1.0 |
| TEGO ® SML 20 | 3.0 | 4.0 | 3.0 | 4.0 | 3.0 | 4.0 | 3.0 | 4.0 |
| Teginacid ® H | 3.0 | 3.0 | 3.0 | 3.0 | 3.0 | 3.0 | 3.0 | 3.0 |
| TEGO ® Alkanol 18 | 1.0 | 1.0 | 1.0 | 1.0 | 1.0 | 1.0 | 1.0 | 1.0 |
| ABIL ® 350 | 0.5 | 0.5 | 0.5 | 0.5 | 0.5 | 0.5 | 0.5 | 0.5 |
| Tegosoft ® Liquid | 4.0 | 4.0 | 4.0 | 4.0 | 4.0 | 4.0 | 4.0 | 4.0 |
| Tegosoft ® CT | 4.0 | 4.0 | 4.0 | 4.0 | 4.0 | 4.0 | 4.0 | 4.0 |
| Phase B |  |  |  |  |  |  |  |  |
| Water | ad 100 | ad 100 | ad 100 | ad 100 | ad 100 | ad 100 | ad 100 | ad 100 |
| Glycerol | 3.0 | 3.0 | 3.0 | 3.0 | 3.0 | 3.0 | 3.0 | 3.0 |
| Phase C |  |  |  |  |  |  |  |  |
| Reach ® 501 | — | — | — | — | 20.0 | 20.0 | 20.0 | 20.0 |
| Kathon ™ CG | 0.03 | 0.03 | 0.03 | 0.03 | 0.03 | 0.03 | 0.03 | 0.03 |
| Fragrance | 0.5 | 0.5 | 0.5 | 0.5 | 0.5 | 0.5 | 0.5 | 0.5 |

EXAMPLE 17

Roll-On Emulsions

|  | RE-1 | RE-2 | RE-3 | RE-4 | RE-7 | RE-8 | RE-9 | RE-10 |
|---|---|---|---|---|---|---|---|---|
| Phase A |  |  |  |  |  |  |  |  |
| Example 1 | 0.3 | 1.0 | — | — | 0.3 | 1.0 | — | — |
| Example 8 | — | — | 0.3 | 1.0 | — | — | 0.3 | 1.0 |
| TEGO ® SML 20 | — | — | — | — | — | — | — | — |
| TEGO ® Alkanol S2P | 2.2 | 2.2 | 2.2 | 2.2 | 2.2 | 2.2 | 2.2 | 2.2 |
| TEGO ® Alkanol S20P | 1.0 | 1.0 | 1.0 | 1.0 | 1.0 | 1.0 | 1.0 | 1.0 |
| Tegosoft ® Liquid | 2.0 | 2.0 | 2.0 | 2.0 | 2.0 | 2.0 | 2.0 | 2.0 |
| Varonic ® APS | 2.0 | 2.0 | 2.0 | 2.0 | 2.0 | 2.0 | 2.0 | 2.0 |
| ABIL ® 350 | 0.5 | 0.5 | 0.5 | 0.5 | 0.5 | 0.5 | 0.5 | 0.5 |
| Phase B |  |  |  |  |  |  |  |  |
| Water | ad 100 | ad 100 | ad 100 | ad 100 | ad 100 | ad 100 | ad 100 | ad 100 |
| Glycerol | 3.0 | 3.0 | 3.0 | 3.0 | 3.0 | 3.0 | 3.0 | 3.0 |
| Phase C |  |  |  |  |  |  |  |  |
| Reach ® 501 | — | — | — | — | 30.0 | 30.0 | 30.0 | 30.0 |
| Kathon ™ CG | 0.03 | 0.03 | 0.03 | 0.03 | 0.03 | 0.03 | 0.03 | 0.03 |
| Fragrance | 0.5 | 0.5 | 0.5 | 0.5 | 0.5 | 0.5 | 0.5 | 0.5 |

EXAMPLE 18

Deodorant Sticks without ACH

|  | ST-1 | ST-2 | ST-3 | ST-4 |
|---|---|---|---|---|
| Phase A |  |  |  |  |
| Varonic ® APM | 77.5 | 77.5 | — | — |
| Propylene Glycol | 10.0 | 10.0 | 28.5 | 28.5 |
| Butylene Glycol | — | — | 20.0 | 20.0 |
| Sodium Stearate | 8.0 | 8.0 | 8.0 | 8.0 |
| Water | 3.0 | 3.0 | 8.0 | 8.0 |
| Phase B |  |  |  |  |
| Fragrance | 1.0 | 1.0 | 1.0 | 1.0 |
| Example 1 | 0.5 | — | 0.5 | — |
| Example 8 | — | 0.5 | — | 0.5 |
| Water | ad 100 | ad 100 | ad 100 | ad 100 |
| Ethanol | — | — | 34.0 | 34.0 |

EXAMPLE 19

Deodorant Sticks with ACH

|  | ST-5 | ST-6 |
| --- | --- | --- |
| Phase A |  |  |
| TEGO ® Alkanol 18 | 23.5 | 23.5 |
| Hydrogenated Castor Oil | 4.0 | 4.0 |
| Tegosoft ® PBE | 10.0 | 10.0 |
| Tegosoft ® P | 16.0 | 16.0 |
| TEGO ® Alkanol L4 | 1.0 | 1.0 |
| Phase B |  |  |
| Cyclopentasiloxane | 20.0 | 20.0 |
| Phase C |  |  |
| Micro-Dry ® Ultrafine | 20.0 | 20.0 |
| Phase D |  |  |
| Fragrance | 1.0 | 1.0 |
| Example 1 | 0.5 | — |
| Example 8 | — | 0.5 |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A compound of general formula (I)

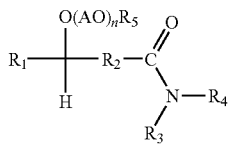

(I)

wherein $R_1=CH_3$, $R_2$ is a direct bond, $R_3=H$, $R_4=C_8$ alkyl, $R_5=H$, and n=0, or wherein $R_1=CH_3$, $R_2$ is a direct bond, $R_3=H$, $R_4=C_8$ alkyl, $R_5=H$ or acyl, n is 2 to 5, based on the mean value of all oligomers, and $AO=-CH_2CH_2O-$.

2. A method of controlling Gram-positive microorganisms in a cosmetic preparation comprising adding at least one microorganism controlling compound to said cosmetic preparation, said at least one microorganism controlling compound is a compound of general formula Ia

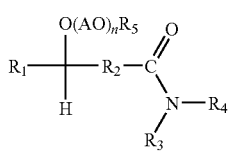

(Ia)

wherein $R_1$=H or a hydrocarbon radical having 1 to 18 carbon atoms, $R_2$=a direct bond or a hydrocarbon radical having 1 to 18 carbon atoms, $R_3$, $R_4$=independently of one another, is H or a hydrocarbon radical having 1 to 18 carbon atoms, $R_5$=H or $C_1$-$C_4$-acyl radical, AO=at least one radical selected from the group $-CH_2CH_2O-$, $-CH_2CHR_6O-$, $-CHR_6CH_2O-$, and $-CH_2CH_2OHCH_2O-$ where $R_6=C_1$-$C_4$-alkyl, n=0 to 20, based on the mean value of all oligomers, with the proviso that $R_3$ and $R_4$ are not H at the same time and the sum of the carbon atoms in $R_3$ and $R_4$ is not greater than 18 and that the sum of the carbon atoms in $R_1$, $R_2$, $R_3$ and $R_4$ does not exceed 36.

3. The method as claimed in claim 2, wherein said hydrocarbon of one of $R_1$, $R_2$, $R_3$ and $R_4$ is branched and/or contains multiple bonds and/or hydroxy groups and/or alkyl groups and/or hydroxyalkyl groups.

4. The method as claimed in claim 2 wherein n=0 to 20, $R_5$=H, $R_1$=H or $CH_3$, $R_2$ is a direct bond or a hydrocarbon radical having 1 to 4 carbon atoms which optionally contains hydroxyalkyl groups, $R_3$=H and $R_4$=$C_4$-$C_{12}$-alkyl radical.

5. The method as claimed in claim 2, wherein $AO=-CH_2CH_2O-$ and n=2 to 5.

6. The method as claimed in claim 5 wherein said Gram-positive microorganisms are coryneform bacteria.

7. A formulation for the selective control of microorganisms, comprising at least one compound of general formula (Ia)

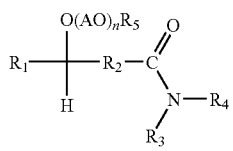

(Ia)

wherein $R_1$=H or a hydrocarbon radical having 1 to 18 carbon atoms, $R_2$=a direct bond or a hydrocarbon radical having 1 to 18 carbon atoms, $R_3$, $R_4$=independently of one another, is H or a hydrocarbon radical having 1 to 18 carbon atoms, $R_5$=H or $C_1$-$C_4$-acyl radical, AO=at least one radical selected from the group $-CH_2CH_2O-$, $-CH_2CHR_6O-$, $-CHR_6CH_2O-$, and $-CH_2CH_2OHCH_2O-$ where $R_6=C_1$-$C_4$-alkyl, n=0 to 20, based on the mean value of all oligomers, with the proviso that $R_3$ and $R_4$ are not H at the same time and the sum of the carbon atoms in $R_3$ and $R_4$ is not greater than 18 and that the sum of the carbon atoms in $R_1$, $R_2$, $R_3$ and $R_4$ does not exceed 36.

8. The formulation as claimed in claim 7, wherein said hydrocarbon of one of $R_1$, $R_2$, $R_3$ and $R_4$ is branched and/or contains multiple bonds and/or hydroxy groups and/or alkyl groups and/or hydroxyalkyl groups.

9. The formulation as claimed in claim 7, which comprises 0.001 to 10% by weight of at least one compound of said general formula (Ia).

10. The formulation as claimed in claim 7, which is a deodorant in the form of an aerosol spray, pump spray, roll-on formulation, deodorant stick, W/O or O/W emulsion or wipe.

11. The formulation as claimed in claim 7, which is an oral hygiene product.

12. A method of combating acne/dandruff comprising applying a formulation including at least one antiacne/antidandruff compound to skin or hair, said at least one antiacne/antidandruff compound is a compound of general formula Ia

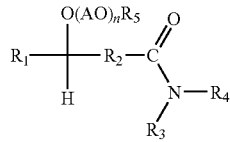

(Ia)

wherein $R_1$=H or a hydrocarbon radical having 1 to 18 carbon atoms, $R_2$=a direct bond or a hydrocarbon radical having 1 to 18 carbon atoms, $R_3$, $R_4$=independently of one another, is H or a hydrocarbon radical having 1 to 18 carbon atoms, $R_5$=H or $C_1$-$C_4$-acyl radical, AO=at least one radical selected from the group —$CH_2CH_2O$—, —$CH_2CHR_6O$—, —$CHR_6CH_2O$—, and —$CH_2CH_2OHCH_2O$— where $R_6$=$C_1$-$C_4$-alkyl, n=0 to 20, based on the mean value of all oligomers, with the proviso that $R_3$ and $R_4$ are not H at the same time and the sum of the carbon atoms in $R_3$ and $R_4$ is not greater than 18 and that the sum of the carbon atoms in $R_1$, $R_2$, $R_3$ and $R_4$ does not exceed 36.

13. A method of controlling Gram-positive microorganisms comprising applying a cosmetic preparation to skin, said cosmetic preparation including a compound of general formula (Ia)

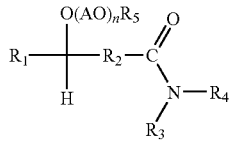

(Ia)

wherein $R_1$=H or a hydrocarbon radical having 1 to 18 carbon atoms, $R_2$=a direct bond or a hydrocarbon radical having 1 to 18 carbon atoms, $R_3$, $R_4$=independently of one another, is H or a hydrocarbon radical having 1 to 18 carbon atoms, $R_5$=H or $C_1$-$C_4$-acyl radical, AO=at least one radical selected from the group —$CH_2CH_2O$—, —$CH_2CHR_6O$—, —$CHR_6CH_2O$—, and —$CH_2CH_2OHCH_2O$— where $R_6$=$C_1$-$C_4$-alkyl, n=0 to 20, based on the mean value of all oligomers, with the proviso that $R_3$ and $R_4$ are not H at the same time and the sum of the carbon atoms in $R_3$ and $R_4$ is not greater than 18 and that the sum of the carbon atoms in $R_1$, $R_2$, $R_3$ and $R_4$ does not exceed 36.

* * * * *